United States Patent [19]

Nakabayashi et al.

[11] Patent Number: 5,766,328
[45] Date of Patent: Jun. 16, 1998

[54] DENTAL COMPOSITION FOR RELIEVING DENTIN HYPERSENSITIVITY

[75] Inventors: Nobuo Nakabayashi, 5-6-20, Koganehara., Matsudo Chiba-ken 270; Takashi Yamamoto, Moriyama; Yasukazu Saimi, Moriyama; Masami Arata, Moriyama; Harumi Tanaka, Moriyama, all of Japan

[73] Assignees: Sun Medical Co., Ltd., Moriyama; Nobuo Nakabayashi, Chiba, both of Japan

[21] Appl. No.: 788,566

[22] Filed: Jan. 24, 1997

Related U.S. Application Data

[63] Continuation of Ser. No. 571,219, Dec. 12, 1995, abandoned.

[30] Foreign Application Priority Data

Dec. 13, 1994 [JP] Japan .................... 6-308666

[51] Int. Cl.$^6$ .............. C08F 2/26; A61K 6/00; C09J 133/06; C09J 133/12
[52] U.S. Cl. .............. 106/35; 424/49; 424/56; 424/57; 514/128; 514/579
[58] Field of Search .............. 106/35; 424/49, 424/56, 57; 514/128, 579

[56] References Cited

U.S. PATENT DOCUMENTS

4,057,621  11/1977  Pashley et al. ............ 424/49

FOREIGN PATENT DOCUMENTS

| 0572227 | 12/1993 | European Pat. Off. . |
|---|---|---|
| 572227 | 12/1993 | European Pat. Off. . |
| 4217904 | 8/1992 | Japan . |
| 5070358 | 3/1993 | Japan . |
| 5255029 | 10/1993 | Japan . |
| 6116153 | 4/1994 | Japan . |
| 6145020 | 5/1994 | Japan . |
| 2239601 | 7/1991 | United Kingdom . |
| WO92/04006 | 3/1992 | WIPO . |
| WO93/13748 | 7/1993 | WIPO . |
| WO96/14825 | 5/1996 | WIPO . |

*Primary Examiner*—Melissa Bonner
*Attorney, Agent, or Firm*—Sherman and Shalloway

[57] ABSTRACT

There is provided a dental composition for relieving dentin hypersensitivity comprising (A) an aqueous emulsion component which contains, as emulsion particles, polymer particles having a diameter smaller than that of a dentinal tubule and forming an agglomerate larger than the diameter of a dentinal tubule when they react with a calcium compound, and (B) a water-soluble organic acid component or a water-soluble salt component thereof, a calcium salt of the organic acid being insoluble or hardly soluble in water. Using this composition, dentinal tubules open to the surface of dentin are occluded to relieve dentin hypersensitivity immediately and lastingly.

8 Claims, No Drawings

DENTAL COMPOSITION FOR RELIEVING DENTIN HYPERSENSITIVITY

This application is a continuation of application Ser. No. 08/571,219, filed Dec. 12, 1995, now abandoned.

BACKGROUND OF THE INVENTION

1. Field of the Invention

This invention relates to a dental composition for occluding dentinal tubules. More specifically, it relates to a dental composition for relieving dentin hypersensitivity which induces pain sensations caused by cold water, hot water, sweet, acidic foods and scraping, by occluding dentinal tubules. Further, it relates to a dental composition which can be preserved stably and hygienically.

2. Prior Art

Cold and heat pain sensations which are encountered when your tooth is brought into contact with air or water having different temperature from body temperature, sweet and acid taste pain sensations which are encountered when you have sweet and acid foods, a scraping pain sensation which is encountered when your tooth is brought into contact with a toothbrush or like, and others are caused by dentin hypersensitivity or pulpitis.

Pulpitis occurs as the result of inflammation caused by the infection of dental pulp with bacteria, and its pain sensation is continued for a relatively long period and can be treated only by removing the dental pulp.

Meanwhile, dentin hypersensitivity is a temporary induced pain sensation produced by physical or chemical stimulus. Therefore, a technique for easing the nerve cell of pulp whose reaction to stimulus is hypersensitive and a technique for excluding external stimulus to dental pulp have been proposed as a measure to overcome dentin hypersensitivity.

Pashley et al. propose in the specification of U.S. Pat. No. 4,057,621 a dental composition for relieving hypersensitivity which comprises an oxalate of a mono- or bi-substituted alkali metal or ammonium in a concentration range of from 2% by weight to saturation as well as a technique for relieving hypersensitivity.

In JP-A-4-217904 (the term "JP-A" as used herein means an "unexamined published Japanese patent application), Imai et al. propose a dental treatment composition for forming a precipitate by sequentially applying two liquids A and B containing substances which generate a hardly soluble precipitate when mixed together. In this proposal, liquid A is an aqueous solution containing 1 to 70% of a sodium salt, potassium salt or lithium salt of an inorganic or organic acid, and liquid B is a mixture containing at least one selected from the group consisting of chlorides, nitrates, sulfates and acetates of calcium, zinc, strontium, magnesium, aluminum, barium, iron, copper, silver, lead and tin, or an aqueous solution containing 1 to 70% of calcium chloride, zinc chloride or strontium chloride.

JP-A-6-145020 proposes a crystal forming primer for crystal generating teeth, which comprises (A) a solution of 1 to 35% potassium oxalate, (B) aluminum oxalate and (C) 2% nitric acid.

JP-A-5-70358 proposes a treatment agent for dentin hypersensitivity containing the following components (A) and (B). The component (A) is colloidal zinc hydroxide and/or zinc oxide obtained by mixing a water-soluble zinc salt and a polyol phosphoric acid ester and/or a salt thereof in an aqueous medium, and the component (B) is a zinc salt of a polyol phosphoric acid ester.

In JP-A-5-255029, Imai et al. propose a dental treatment composition for forming a precipitate by sequentially applying two liquids A and B containing substances capable of producing fluoroapatite swiftly when mixed together. In this respect, the liquid A contains a water-soluble phosphoric acid salt in a concentration of 1 to 30% and a water-soluble fluoride in an amount of 0.01 to 5% by weight, and the liquid B contains a water-soluble calcium salt in an amount of 1 to 30% by weight.

JP-A-6-116153 proposes a coating agent for relieving hypersensitivity which consists of a first liquid containing an aluminum compound and a second liquid containing at least one compound selected from the group consisting of phosphoric acid compounds, oxalic acid compounds, silicic acid compounds, fluorides and compounds providing alkalinity. This proposal is aimed to precipitate a precipitate in dentinal tubules which are open to the exposed surface of dentin and occlude the dentinal tubules by applying a solution of a compound or composition for forming a precipitate on the surface of a tooth. It also makes use of the effect of alleviating the activity of sensory nerves with a certain compound such as a potassium ion.

However, it has been difficult to newly form on the surface of dentin a predetermined amount of a precipitate large enough to occlude a dentinal tubule which is said to have a diameter of 1 to 3 μm because of impedient conditions such as the properties of a tooth and a sanitary state of the surface of dentin. To attain this purpose, a long-time treatment and repetitions of a treatment have been employed and patients have suffered more pain in these treatments.

A technique for easing the nerve cell of pulp is aimed to paralyze or ease the nerve cell which is made hypersensitive by a medicine or the like. However, its mechanism has not been elucidated thoroughly. One of the means of excluding external stimuli from dental pulp is to occlude dentinal tubules for connecting the outside and the dental pulp, and as described above, there is a proposal for occluding dentinal tubules with a precipitate formed on the surface of a tooth as described above. However, formation of a precipitate or precipitation of a precipitate in a dentinal tubule could not be carried out satisfactorily depending on the opening conditions of the dentinal tubule near the surface of dentin and the properties of a tooth, thereby making it impossible to keep occlusion stably for a prolonged time.

In JP-A-6-57080, Nakabayashi et al. propose an emulsion of a polymer which comprises a recurring unit derived from a (meth)acrylic acid ester and a recurring unit derived from a vinyl compound having a functional group —$SO_3R$ (R is hydrogen atom, an alkali metal or an ammonium ion) and a method for relieving dentin hypersensitivity using the same. Advantages obtained by applying a polymer emulsion to dentin hypersensitivity are (1) a large amount of a polymer can be applied with a relatively low-viscosity liquid and (2) a film formed of the polymer becomes insoluble in water when it is dried. Since a solvent for an aqueous emulsion of a polymer is water, there are almost no handling problems such as toxicity and ventilation.

SUMMARY OF THE INVENTION

The inventors of the present invention have conducted additional experiments based on the above proposal made by Nakabayashi et al., and have observed the effect of relieving hypersensitivity in 15 out of 17 patients having dentin hypersensitivity. However, a remarkable relieving effect was not observed in the remaining 2 patients. The inventors have conducted intensive studies on the cause of no effect and found that the amount of an emulsion charged into a dentinal tubule and the stability (retention) of a formed film differ depending on the opening conditions of the dentinal tubule and the location and properties of dentin. In other words, when the opening of the dentinal tubule is small, the emulsion may not be thoroughly charged into the tubule. Further, when the content of hydroxyapatite such as deep dentin and root dentin is small, adhesion of the formed film to the surface of dentin and retention of adhesion may be insufficient.

It is therefore an object of the present invention to provide a dental composition which is for use in relieving dentin hypersensitivity by occluding dentinal tubules.

It is another object of the present invention to provide a dental composition capable of occluding a dentinal tubule even when the tubule has a small diameter.

It is a further object of the present invention to provide a dental composition which can relieve hypersensitivity immediately and for a prolonged period.

The above objects and advantages of the present invention can be first attained by a dental composition for relieving dentin hypersensitivity comprising (A) an aqueous emulsion component which contains polymer particles as emulsion particles having a diameter smaller than that of a dentinal tubule and forming an agglomerate larger than the diameter of a dentinal tubule when they react with a calcium compound, and (B) a water-soluble organic acid component or a water-soluble salt component thereof, a calcium salt of the organic acid being insoluble or hardly soluble in water.

The above objects and advantages of the present invention can be secondly attained by dental composition for relieving dentin hypersensitivity comprising (A) an aqueous emulsion component (1) which contains polymer particles as emulsion particles having a diameter smaller than that of a dentinal tubule and forming an agglomerate larger than the diameter of a dentinal tubule when they react with a calcium compound and (2) which has a metal ion concentration in a dispersing medium of 1,000 ppm or less, and (B) a water-soluble organic acid component or a water-soluble salt component thereof, a calcium salt of the organic acid being insoluble or hardly soluble in water.

The other objects and advantages of the present invention will become apparent from the following detailed description of the invention.

DETAILED DESCRIPTION OF THE INVENTION component (A) is a polymer emulsion (hereinafter sometimes referred to as "latex") prepared by emulsifying or dispersing a natural resin or a synthetic resin into water. The component (A) is characterized in that the emulsified or dispersed polymer contains emulsion particles having a particle diameter smaller than the diameter of a dentinal tubule and that the polymer can form an agglomerate having a diameter larger than that of a dentinal tubule when it reacts with a calcium compound.

In order to make an aqueous emulsion penetrate to a depth sufficient for occluding dentinal tubules, the particle diameter of the emulsion particle of the polymer must be smaller than the diameter of a dentinal tubule. The diameter of a dentinal tubule differs depending on its location and depth and by each tubule, but it is generally in the range of 1 to 3 μm. Therefore, the average particle diameter of the emulsion particle of the polymer contained in the component (A) is preferably 3 μm or less, more preferably 1 μm or less.

The diameter of a dentinal tubule can be generally measured by observing through a scanning electron microscope (SEM) the surface of dentin exposed by cutting out the enamel of a removed tooth which has been brushed with a toothbrush and dentifrice for 1 minute or more and then subjected to ultrasonic cleaning in water.

There is a distribution for the particle diameters of the emulsion particles of the component (A) and all the emulsion particles do not need to have a particle diameter smaller than the diameter of a dentinal tubule. Preferably, emulsion particles having a particle diameter of less than 3 μm account for 50% or more by weight of the total of all the emulsion particles contained in the component (A), and, more preferably, all the emulsion particles have a particle diameter of less than 3 μm. In addition to the above condition, particularly preferably, emulsion particles having a particle diameter of 1 μm or less account for 65% or more by weight, more preferably 75% or more by weight. The object of the present invention can be attained by emulsion particles having the above particle diameter distribution.

The polymer usable as the component (A) of the present invention is homopolymers or copolymers synthesized from radical polymerizable monomers. Illustrative examples of the radical polymerizable monomer include conjugated diene monomers such as butadiene and isoprene; aromatic vinyl monomers such as styrene, a-methylstyrene and chlorostyrene; vinyl cyanide monomers such as acrylonitrile and methacrylonitrile; alkyl (meth)acrylic esters such as methyl (meth)acrylate (hereinafter referred like this as a generic name for acrylic acid and methacrylic acid), ethyl (meth) acrylate and butyl (meth)acrylate; vinyl halides and vinylidenes such as vinyl chloride, vinyl bromide, vinylidene chloride and vinylidene bromide; vinyl esters such as vinyl acetate and vinyl propionate; and the like. These monomers may be used alone or in combination of two or more for polymerization.

Preferably, the polymer synthesized from the above radical polymerizable monomers is chemically bonded to a functional group which reacts with a calcium compound. The functional group which reacts with a calcium compound is at least one selected from the group consisting of a carboxyl group, a group having at least one hydroxyl group bonded to a phosphorus atom, and a sulfonic acid group. Methods for introducing the above functional group include one for introducing a functional group into a polymer, typified by a polystyrene sulfonating method and one for hydrolyzing a polymer containing a carboxylate or phosphate. An alternative preferred method is to copolymerize the above radical polymerizable monomer and a radical polymerizable monomer having the above functional group or a functional group which can be easily converted into the above functional group in water. Illustrative examples of the radical polymerizable monomer having a functional group which reacts with a calcium compound are given below.

Illustrative examples of the radical polymerizable monomer having a carboxyl group or a functional group which can be easily converted into a carboxyl group in water include monocarboxylic acids, dicarboxylic acids, tricarboxylic acids, tetracarboxylic acids, and salts and anhydrides thereof, such as (meth)acrylic acid, maleic acid, p-vinylbenzoic acid, 11-(meth)acryloyloxy-1, 1-undecanedicarboxylic acid (MAC-10), 1, 4-di(meth) acryloyloxyethylpyromellitic acid, 6(meth) acryloyloxyethylnaphthalene-1,2,6-tricarboxylic acid, 4-(meth)acryloyloxymethyltrimellitic acid and an anhydride thereof, 4-(meth)acryloyloxyethyltrimellitic acid and an anhydride thereof, 4-(meth)acryloyloxybutyltrimellitic acid and an anhydride thereof, 4-[2-hydroxy-3-(meth) acryloyloxy]butyltrimellitic acid and an anhydride thereof, 2,3-bis(3,4-dicarboxybenzoyloxy)propyl (meth)acrylate, N,O-di(meth)acryloyloxytyrosine, O-(meth) acryloyloxytyrosine, N-(meth)acryloyloxytyrosine, N-(meth)acryloyloxyphenylalanine, N-(meth)acryloyl-p-aminobenzoic acid, N-(meth)acryloyl-O-aminobenzoic acid, 2-, 3- or 4-(meth)acryloyloxybenzoic acid, adduct of 2-hydroxyethyl (meth)acrylate with pyromellitic dianhydride (PMDM), adduct of 2-hydroxyethyl (meth)acrylate with maleic anhydride or 3,3', 4,4'-benzophenonetetracarboxylic dianhydride (BTDA) or 3,3', 4,4'-biphenyltetracarboxylic dianhydride, adduct of 2-(3,4-dicarboxybenzoyloxy)1,3-di(meth)acryloyloxypropane, N-phenylglycine or N-tolyl glycine with glycidyl (meth) acrylate, 4-[(2-hydroxy-3-(meth)acryloyloxypropyl)amino] phthalic acid, 3- or 4-[N-methyl-N-(2-hydroxy-3 (meth) acryloyloxypropyl)amino]phthalic acid and the like. Among these, preferred are 11-methacryloyloxy-1, 1-undecanedicarboxylic acid (MAC-10) and 4-methacryloyloxyethyltrimellitic acid (4-MET) and an anhydride thereof (4-META).

Preferred examples of the group having at least one hydroxyl group bonded to a phosphorus atom and the functional group which can be easily converted into the above group in water include phosphoric ester groups having one or two hydroxyl groups and salts thereof. Illustrative examples of the polymerizable monomer having such a group include 2-(meth)acryloyloxyethylacid phosphate, 2- or 3-(meth)acryloyloxypropylacid phosphate, 4-(meth) acryloyloxybutylacid phosphate, 6-(meth) acryloyloxyhexylacid phosphate, 8-(meth) acryloyloxyoctylacid phosphate, 10-(meth) acryloyloxydecylacid phosphate, 12-(meth) acryloyloxydodecylacid phosphate, bis{2-(meth) acryloyloxyethyl}acid phosphate, bis{2- or 3-(meth) acryloyloxypropyl}acid phosphate, 2-(meth) acryloyloxyethylphenylacid phosphate, 2-(meth) acryloyloxyethyl-p-methoxyphenylacid phosphate and the like. Compounds in which the phosphoric acid group contained in the above compounds is substituted with a thiophosphoric acid group are also included in these examples. Among these, preferred are 2-(meth) acryloyloxyethylphenylacid phosphate and 10-(meth) acryloyloxydecylacid phosphate.

Illustrative examples of the polymerizable monomer having a sulfonic acid group or a functional group which can be easily converted into a sulfonic acid group in water include 2-sulfoethyl (meth)acrylate, 2- or 1-sulfo-1 or 2-propyl (meth)acrylate, 1- or 3-sulfo-2-butyl (meth)acrylate, 3-bromo-2-sulfo-2-propyl (meth)acrylate, 3-methoxy-1-sulfo-2-propyl (meth)acrylate, 1,1-dimethyl-2-sulfoethyl (meth)acrylamide, styrene sulfonic acid and salts thereof, of which, 2-methyl-2-(meth)acrylamidepropanesulfonic acid, styrene sulfonic acid and salts thereof are preferred.

The number average molecular weight Mn, measured by a GPC method, of the polymer contained in the component (A) is usually 3,000 or more, preferably 7,000 or more, more preferably 10,000 or more. The upper limit of the number average molecular weight is generally 5,000,000. The component (A) may contain the polymer as an emulsion particle in an amount of 0.1 to 60% by weight, preferably 0.5 to 40% by weight, more preferably 1 to 20% by weight.

Preferably, the component (A) is an emulsion containing as an emulsion particle a copolymer having alkyl (meth) acrylic ester units having 4 to 8 carbon atoms and styrene sulfonic acid units in a molar ratio of alkyl acrylic ester units to styrene sulfonic acid units of 50/50 to 99.5/0.5, which the copolymer is obtained by a polymerization method not using an emulsifier, i.e., a so-called soap-free emulsion polymerization. As this copolymer emulsion, the one proposed in JP-A-6-57080 can be used. A more preferred example is a component (A) prepared by forming emulsion particles of the copolymer having a diameter of 3 µm or less, preferably 1 µm or less, more preferably 0.5 µm or less, with a dispersion grinder such as a high-speed mixer or a homogenizer such that the emulsion particles are contained in the component (A) in an amount of 0.5% or more by weight thereby to improve the dispersion stability. Above all, emulsion particles of the copolymer having a particle diameter of 1.0 µm or less preferably account for 50% by weight, more preferably 75% or more by weight, the most preferably 100% by weight of the total of emulsion particles.

The emulsion particle having a particle diameter smaller than that of a dentinal tubule, contained in the component (A), is able to form an agglomerate having a diameter larger than that of the dentinal tubule through its reaction with a calcium compound when a calcium compound such as calcium chloride is added to the component (A). The diameter of the agglomerate is generally more than 3 µm, preferably 10 µm or more, more preferably 50 µm to several thousands µm.

The addition of the calcium compound is in the range of 10 to 100 parts by weight based on 100 parts of an nonvolatile component contained in the emulsion.

Using the component (A) having the above properties in the composition of the present invention, a small sized emulsion particle penetrating into a dentinal tubule reacts with a calcium ion eluted from hydroxyapatite present in dentin that forms dentinal tubules or a calcium ion present in a marrow liquid contained in dentin to form a great number of large agglomerates. The great number of large agglomerates thus formed are laid continuously in the longitudinal directions of the dentinal tubules as a coating film. The tubules are occluded by the formation of the coating films. The formation of these occluded tubules is made quickly by using the component (B) of the present invention and kept for a prolonged period because adhesion between the agglomerate and dentin is maintained for a long time.

The nonvolatile component in the component (A) is contained in an amount of 0.1 to 60 parts by weight, preferably 0.5 to 40 parts by weight, more preferably 1 to 20 parts by weight, based on 100 parts by weight of the dental composition.

The component (B) of the composition of the present invention serves to control the agglomeration speed of emulsion particles contained in the component (A), that is, the speed of forming hardly soluble gels (agglomerates), and to improve the durability of a coating film formed of the hardly soluble gel by allowing the component (B) to form a calcium salt which is insoluble or hardly soluble in water.

The calcium salt of the component (B) is a crystal in various forms. It is generally spherical, relatively roundish oval, laminar or needle-shaped. Although its size differs depending on the form of a crystal, a spherical or roundish oval crystal has an average diameter of 0.1 to 10 µm, a laminar crystal has an average side length of 0.1 to 10 µm, and a needle-shaped crystal has a thickness of 0.1 to 5 µm and a length of 1 to 10 µm. The calcium salt having such forms is present on the surface of dentin and in dentinal tubules together with a hardly soluble gel generated from the component (A) and serves to promote the occlusion of the dentinal tubules and to reduce volume shrinkage at the time of the formation of the hardly soluble gel or drying.

The component (B) in the present invention is a water-soluble organic acid or a water-soluble salt thereof. The calcium salt of the organic acid is a salt which is insoluble or hardly soluble in water. Water insolubility or difficulty of being soluble in water is judged by the presence or absence of a precipitate generated when a solution containing the component (B) and a solution containing calcium are mixed together. The presence or absence of the precipitate can be known by the relationship between solubility product and ion product. That is, when the ion product of the calcium salt of the component (B) is equal to or larger than a solubility product, the calcium salt is considered as insoluble or hardly soluble in water.

For the simple measure for the generation of a precipitate, there is a visual method for observing the generation of a precipitate when an aqueous solution containing 1 to 5% by weight of a water-soluble organic acid or a water-soluble salt component thereof and an aqueous solution containing the same volume range of calcium chloride are mixed together.

The component (B) in the present invention can include oxalic acid or a water-soluble oxalic acid salt selected from the group consisting of oxalic acid, and metal salts, ammonium salts and amine salts of oxalic acid, or propionic acid or a water-soluble propionic acid salt selected from the group consisting of propionic acid, and metal salts, ammonium salts and amine salts of propionic acid.

The measure for water solubility is that water solubility at 25° C. should be 0.5 g/100 ml or more. Specific examples of the water-soluble oxalic acid compound include oxalic acid, hydrogen sodium oxalate, sodium oxalate, hydrogen potassium oxalate, potassium oxalate, hydrogen lithium oxalate, lithium oxalate, hydrogen ammonium oxalate, ammonium oxalate, aniline oxalate, zinc potassium oxalate, aluminum oxalate, aluminum ammonium oxalate, aluminum sodium oxalate, antimony potassium oxalate, chromium potassium oxalate, hydrogen barium oxalate, iron potassium oxalate and the like. Among these, preferred are oxalic acid, hydrogen potassium oxalate and iron potassium oxalate.

In the present invention, when the component (A) is contained preferably in an amount of 50 to 99.5 parts by weight, more preferably 70 to 99 parts by weight, the most preferably 90 to 98 parts by weight, based on 100 parts by weight of the total of the components (A) and (B), the effect of the present invention is exhibited remarkably.

The proportion of the component (B) affects the size and the amount of precipitation of the calcium salt of the component (B). If the amount of precipitation is small or the crystal size is too small with a proportion below the above range, an expected effect may not be exhibited fully. On the other hand, if the proportion of the component (B) is beyond the above range, the calcium salt may be precipitated from the solution or agglomerate the emulsion particles considerably when it reaches its saturation.

As for how to use the composition comprising the components (A) and (B),
(1) both the components (A) and (B) are mixed together and kept in a container, and the resulting mixture is applied to form a coating film, or
(2) a composition comprising the component (A) kept in a container A and a composition comprising the component (B) kept in a container B are applied sequentially in a desired order or mixed together immediately before use and applied to form a coating film.

To the dental composition of the present invention may be added an agglomeration promoting agent in a concentration range that does not impair the effect of the present invention. Illustrative examples of the agglomeration promoting agent include inorganic acids such as hydrochloric acid and nitric acid; chlorides and oxides of iron, copper, zinc, strontium, silver and tin; organic acids such as formic acid, acetic acid, lactic acid, citric acid, itaconic acid, maleic acid, succinic acid, malic acid, tannic acid, toluene sulfonic acid, adipic acid, tartaric acid and ascorbic acid; EDTA and metal salts thereof; and the like. A fluoride such as sodium fluoride or potassium fluoride may also be used as required. And, inorganic or organic calcium salts such as calcium chloride, calcium hydroxide, calcium bicarbonate, calcium carbonate, calcium oxide, calcium hydrogen phosphate, calcium phosphate, hydroxyapatite or the like may be also used in a concentration range not impairing the effect of the invention.

Further studies conducted by the inventors have revealed that the durability of a coating film of a composition comprising the components (A) and (B) of the present invention formed on the surface of dentin is affected by the concentration of metal ions contained in the dispersing medium of an emulsion, and that the higher the concentration of metal ions the lower the durability becomes. The inventors have therefore studied the metal ions contained in the dispersing medium of the emulsion and the durability of the coating film and have found that a coating film having excellent durability can be obtained by purifying the emulsion to reduce the concentration of metal ions preferably to 1,000 ppm or less, more preferably 800 ppm or less, the most preferably 500 ppm or less.

To reduce the concentration of metal ions to the above low level, a diafiltration method using an ultra-filtration apparatus or a dialysis method can be used. Of these methods, the above diafiltration method is preferred.

The diafiltration method using an ultrafiltration apparatus is used as one of membrane filtration and membrane separation techniques in food, medicine and other industrial fields. An ultrafiltration apparatus and membrane are described in *Outline of Membrane Treatment Technology* edited by Hiroshi Shimizu, supervised by Masayuki Nakagaki and published by Fuji Technosystem Publication Co.

The apparatus described in the above publication can be used in the present invention. An ultrafiltration apparatus and membrane described in Recent *Application of Flat Membrane-type Ultrafiltration Apparatus* written by Suguru Higasa in the December 1990 issue of Gekkan Food Chemical can also be used. More specifically, PC Cassette System manufactured by Rhone Poulenc can be used. Illustrative examples of a material for a cassette-like membrane include polyacrylonitrile copolymers, polyvinylidene fluoride, sulfonated polysulfone, polyether sulfone and the like, of which, sulfonated polysulfone is preferred.

Water usable to reduce the concentration of metal ions contained in the dispersion medium of the emulsion in the present invention is selected from distilled water, deionized water, purified water and the like. Water called "strongly oxidized water" or "strong acid water", obtained by electrolysis of water, can also be used. The above water preferably has a metal ion concentration of 100 ppm or less, more preferably 10 ppm or less, the most preferably 1 ppm or less.

Further, in the present invention, considering that the composition is used in the oral cavity, water which conforms to medical and food standards such as water conforming to the standards of the Japanese Medical Law or water authorized as a food additive is preferably used.

Surprisingly, it has newly been found that the component (A) of the present invention can suppress the proliferation of bacteria in addition to its effect of providing excellent film durability by reducing the concentration of metal ions in the dispersing medium to 1,000 ppm or less through the diafiltration method using an ultrafiltration apparatus in particular. That is, it has been revealed that no generation of mold is observed and further transplanted mold is not grown by reducing the concentration of metal ions contained in the dispersing medium of the component (A) to 1,000 ppm or less. Generation and proliferation of such bacteria as mold are not only insanitary but also readily cause generation of a bad smell and destruction of an emulsion due to the agglomeration of emulsion particles disadvantageously.

To prevent generation of bacteria in the emulsion, an antiseptic component (C) can be used. The term "antiseptic" include mildewproofing agents.

Antiseptics usable in the present invention are those which can be generally used industrially. However, antiseptics suitable for the purpose of the present invention should have low toxicity and be sanitary to the human body and should not impair the effect of relieving hypersensitivity without agglomerating emulsion particles significantly for a short or long period. Cohesiveness of emulsion particles is greatly affected by the chemical structure and amount of an antiseptic used. Meanwhile, the effect of an antiseptic is greatly affected by the components and composition of a polymer constituting an emulsion, the concentration of components dissolved in the emulsion such as cations and anions, and pH of the emulsion. Therefore, a combination of antiseptics which satisfies the above three requirements-low toxicity and sanitation to the human body, no agglomeration of emulsion particles and antiseptic effect-should be selected.

Illustrative examples of the antiseptic component (C) which can be suitably used in the dental composition of the present invention include aliphatic alcohols such as ethanol, n-propanol and isopropanol; halogenated aliphatic alcohols such as chlorobutanol and 2-bromo-2-nitro-propanol1-1,3-diol (to be abbreviated as Bronopol hereinafter); aromatic alcohols such as 2,4-dichlorobenzyl alcohol, 2-phenoxyethanol, phenoxyisopropanol, phenylethyl alcohol and 3-(4-chlorophenoxy)-1,2-propane diol; aldehydes such as 5-bromo-5-nitro-1,3-dioxane, formaldehyde, paraformaldehyde and glutaraldehyde; gradually-liberating agent capable of forming an aledehyde such as hexamethylenetetramine, monomethylol dimethyl hydantoin and dimethylol methyl hydantoin under acidic condition; amides such as chloroacetoamide; ureas such as N,N'-methylene-bis(N'-(1-(hydroxymethyl)-2,5-dioxo-4-imidazolidinyl)urea, N-(hydroxymethyl)-N-(1,3-dihydroxymethyl-2,5-dioxo-4-imidazolidinyl)-N'-(hydroxymethyl)urea; inorganic sulfites, bisulfites and pyrosulfites such as sodium sulfite, potassium sulfite, sodium bisulfite, potassium bisulfite, sodium pyrosulfite and potassium pyrosulfite; inorganic acids such as boric acid; organic acid compounds such as formic acid, propionic acid, 10-undecylenic acid, sorbic acid, benzoic acid, salicylic acid and 2-acetyl-5-hydroxy-3-oxo-4-hexanoic acid δ lactone; antibiotics such as 2,6-diacetyl-7,9-dihydroxy-8,9b-dimethyl-1,3-(2H,9bH) dibenzoflane-dione; p-hydroxy benzoate compounds such as benzoate p-hydroxymethyl, benzoate p-hydroxyethyl, benzoate p-hydroxy n-propyl, benzoate p-hydroxy n-isopropyl, benzoate p-hydroxy n-butyl, benzoate p-hydroxy isobutyl, benzoate p-hydroxy t-butyl, and benzoate p-hydroxy benzyl; halogenated phenol compounds such as 4-chloro-3-methyl phenol, 4-chloro-3, 5-xylenol, 3,4,5,6-tetrabromo-O-cresol, 2,4-dichloro-3,5-xylenol, 2-benzyl-4-chloro-phenol, 2,2'-methylene-bis-(4-chlorophenol), 3,3'-dibromo-5,5'-dichloro-2,2'-dihydroxy-diphenylmethane and 2,2'-methylenebis(3,4,6-trichlorophenol); phenol compounds such as 4-chloro-5-methyl-2-(1-methylethyl)phenol, 1-methyl-2-hydroxy-4-isopropyl benzene, 2-phenyl phenol and 4-isopropyl-3-methyl-phenol; diphenyl ether compounds such as 2,4,4'-trichloro-2'-hydroxydiphenyl ether; carbanilide compounds such as 3,4,4'-trichlorocarbanilide and 4,4'dichloro-3-(3-fluoromethyl)carbanilide; benzamidine compounds such as 4,4'-diamidino-α,ω-diphenoxypropane isethionate, 4,4'-(trimethylenedioxy)-bis-(3-bromobenzamidine) isethionate and 1,6-di(4-amidinophenoxy)n-hexane; cyclic thiohydroxamic acids and salts thereof such as pyridine-1-oxide-2-thiol-sodium salts, zinc bis-(2-pyridinethiol-1-oxide)bis-2 (2-pyridylthio)zinc-1,1'-dioxide (Zinc Pyrithione); N-acetal compounds such as 5-amino-1,3-bis(2-ethylhexyl)-5-methylhexahydropyrimidine (Hexetidine) and tris-hydroxyethylhexahydrotriazine; phthalimide derivatives such as N-(trichloromethylthio)-4-cyclohexane-1,2-dicarboxyimide (captane); o-acetal compounds such as 6-acetoxy-2,4-dimethyl-m-dioxane (dimethoxane); oxazolidine compounds such as 4,4-dimethyl-1,3-oxazolidine (oxazine A); quinoline compounds such as 8-hydroxyquinoline; cationic substances such as bis(p-chlorophenyldiguanide)hexane and polyhexamethylenebiguanide hydrochloride; quarterly salt compounds such as alkyltrimethylammonium bromide, N-dodecyl-N,N-dimethylbenzyl ammonium, and N,N-dimethyl-N-(2-(2-(4-(1,1,3,4-tetramethylbutyl)phenoxy)ethoxy)ethyl)-benzene methane ammonium chloride; organic mercury compounds such as ethyl mercury thiosalicylate and phenyl acetate mercury; iodine compounds such as sodium iodate; glyceryl monolaurates; pyridone derivatives such as 1-hydroxy-4-methyl-6-(2,4,4-trimethylpentyl)-2-(1H)pyridone ethanol amine salt; and the like.

An antiseptic which does not impair significant agglomeration of emulsion particles or occlusion of dentinal tubules is preferably selected from among these antiseptics.

An antiseptic suitably used in combination with an emulsion of a copolymer of alkyl (meth)acrylate and styrene sulfonic acid is 2-phenoxy ethanol, benzoic acid or phenethyl alcohol. As for toxicities of these antiseptics and mildewproofing agents, benzoic acid has been finally allowed for use in cosmetics and 2-phenyl alcohol and phenethyl alcohol have been provisionally allowed for use in cosmetics (please refer to "COSMETIC AND DRUG PRESERVATION, PRINCIPLES AND PRACTICE" edited by Jon J. Kabara, published by Fragrance Journal Co.).

The amount of the antiseptic component (C) differs according to the compound and emulsion used, while it is generally used in an amount of 0.01 to 50 parts by weight, preferably in an amount of 0.01 to 20 parts by weight, most preferably in an amount of 0.01 to 10 parts by weight, based on 100 parts by weight of the total of the components (A) and (C).

EXAMPLES

The present invention is explained in more detail hereinunder with reference to the following examples. However, it is to be understood that the invention is not intended to be limited to these examples.

(Preparation of a hypersensitive dentin model)

A bovine lower-jaw anterior tooth which was removed and frozen for preservation was thawed immediately before use, and a dentin plate having about 10×10×2 mm was cut out from the bovine tooth with a low-speed rotary diamond cutter (ISOMET, BUHLER) under injection of water. One side of the dentin plate was brushed with a toothbrush (GUM manufactured by Battler Co.) having dentifrice (WHITE SUNSTAR F manufactured by Sun Star Co.) thereon with a force of 20 to 30 g/cm² for about 2 to 3 minutes under injection of water. After fully washing with water, the dentin plate was applied an ultrasonic wave in water for 10 minutes for washing to prepare a brushed surface as a hypersensitive dentin model. Thereafter, it was preserved in water until it was used in the following experiments. In this preparation, the thus prepared hypersensitive dentin model was used within 24 hours.

(Method for evaluating the effect of relieving hypersensitivity)

Apparent water was removed from the surface of the hypersensitive dentin model taken from water by an air blow and dried. One sponge ball (sponge provided as an accessory of Super Bond C&B, size S) was picked up by tweezers and fully impregnated with the dental composition of the present invention to apply the composition to the surface of the hypersensitive dentin model. The model was left to stand for 20 seconds and dried by an air blow in such a manner that the liquid was not scattered around. A coating film for relieving dentin hypersensitivity was thus formed.

The hypersensitive dentin model having the coating film formed thereon was subjected to an ultrasonic wave in water for 5 minutes (treatment (i)), or brushed with a toothbrush 1,000 times with a load of 100 g under injection of water and washed with water (treatment (ii)). Thereafter, the occlusion of dentinal tubules was observed from a 1,000× scanning electron photomicrograph. The occlusion of dentinal tubules was evaluated by the occlusion degree of dentinal tubules represented by the following equation.

Occlusion degree of dentinal tubules (%)=(Number of occluded dentinal tubules/Total number of dentinal tubules observed)× 100

Yoshiyama et al. calculated an opening degree of dentinal tubules in J. Dent. Res. 68(11), pp.1498–1502, November, 1989 and reported that about 75% of dentinal tubules having hypersensitivity were open whereas only about 25% of dentinal tubules free from hypersensitivity were open. Evaluation was made based on this report. That is, it is evaluated that when the occlusion degree of dentinal tubules was about 75% or more in the present invention, dentin hypersensitivity was fully relieved, and when the occlusion degree was about 25% or less, dentin hypersensitivity was not relieved.

For the above evaluation, only the occlusion of dentinal tubules by a coating film can be evaluated by removing foreign matters adhered to the surface of the coating film through treatment (i). The toothbrush abrasion resistance and occlusion resistance of a coating film can be evaluated through treatment (ii), thereby evaluating film durability in the actual oral cavity.

(Synthesis Example of an emulsion) 50 ml of distilled water was heated to 60° C. and bubbled with a nitrogen gas for 1 hour. Under a nitrogen atmosphere, 2.0 g of methyl methacrylate (MMA), 0.54 g of sodium styrene sulfonate (SSNa), 30 mg of potassium persulfate and 10 mg of sodium hydrogen sulfite were added to the distilled water and stirred violently at 60° C. for 2.5 hours. Further, 1.0 g of MMA, 15 mg of potassium persulfate and 7 mg of sodium hydrogen sulfite were added four times at time intervals of 30 minutes and then stirred violently for 19.5 hours. The resulting mixture was then cooled to room temperature, and 0.19 ml of concentrated hydrochloric acid was added to the mixture and stirred for 2 hours. The mixture was then charged into a dialysis tube to repeat dialysis while the distilled water was exchanged every day during 5 days. This tube was dried at normal temperature under normal pressure to obtain an emulsion having a solid content of 10.9% by weight. It was found from elemental analysis that the MMA unit content of this polymer was 96.9 mol%. When the thus obtained polymer was analyzed by GPC using methyl polymethacrylate whose molecular weight was known as a standard sample, its number average molecular weight (Mn) was found to be $1.0 \times 10_6$. It was confirmed by observation through a transmission microscope that this polymer emulsion had a particle diameter in the range of 0.1 to 0.5 μm and it was also confirmed by laser diffraction/scattering type particle size distribution measuring instrument (LA-910 manufactured by Horiba) that all the polymer emulsion particles had a particle diameter of 1 μm or less. This emulsion is referred to as MSE hereinafter.

Calcium chloride as a calcium compound was added to MSE and stirred. It was observed through a transmission microscope that the polymer emulsion particles agglomerated and the diameters of agglomerates were in the range of 0.1 to 700 μm with a peak ranging from about 0.3 to about 40 μm.

EXAMPLE 1

An emulsion containing 5% by weight of a polymer, prepared by diluting MSE with distilled water, and an aqueous solution of 3% by weight of oxalic acid were kept in separate containers and each 0.05 g fractions were taken from the containers immediately before use and mixed thoroughly to prepare the dental composition of the present invention. The dental composition prepared within 1 minute after mixing was used. As the result, the occlusion degree of dentinal tubules after treatment (i) and treatment (ii) was 100%.

EXAMPLE 2

The affected part was a tooth worn by excess use of a toothbrush. The dental composition of Example 1 was applied to 20 volunteer patients who suffered from dentin hypersensitivity which induced mainly cold water and scraping pain sensations. Since the surface of dentin was relatively clean, it was dried by a mild air blow and then coated with the dental composition of Example 1 in the same manner as in Example 1 to form a coating film. As the result, all the patients did not feel hypersensitivity which induced cold water and scraping pain sensations immediately after the application and during about the past three months.

EXAMPLE 3

The affected part was a dental root exposed by regression of the gum and the dental composition of Example 1 was applied to 10 volunteer patients who suffered from dentin hypersensitivity which induced mainly a cold water pain sensation. Since the surface of dentin was relatively clean, it was dried by a mild air blow and coated with the dental composition of Example 1 in the same manner as in Example 1 to form a coating film. As the result, all the patients did not feel hypersensitivity which induced a cold water pain sensation immediately after the application and during about the past three months.

Comparative Example 1

After treatment (i) and treatment (ii) were carried out without using the dental composition of the present invention in Example 1, the occlusion degree of dentinal tubules was checked and found to be 0% for both treatments (i) and (ii). All dentinal tubules were open.

Comparative Example 2

The procedure of Example 1 was repeated except that only an emulsion containing 5% by weight of a polymer was used in place of the dental composition of the present invention. As the result, the occlusion degree of dentinal tubules after treatment (i) was about 10% and that after treatment (ii) was 0%.

Comparative Example 3

The procedure of Example 3 was repeated except that the emulsion of Comparative Example 2 was used in place of the dental composition of the present invention. That is, the affected part was a dental root exposed by regression of the gum and the above emulsion was applied to 5 volunteer patients who suffered from dentin hypersensitivity which induced mainly a cold water pain sensation. As the result, four out of the five patients did not feel hypersensitivity because the cold water pain sensation was eased immediately after the application but suffered a relapse of dentin hypersensitivity about three or four days later. The effect of relieving hypersensitivity was not observed in one patient immediately after the application.

Comparative Example 4

The procedure of Example 1 was repeated except that only an aqueous solution of 30% by weight of potassium oxalate was used in place of the dental composition of the present invention. As the result, the occlusion degree of dentinal tubules after treatment (i) was about 70% and that after treatment (ii) was 10%.

EXAMPLE 4

The procedure of Emulsion Synthesis Example was repeated to synthesize an emulsion except that a diafiltration using an ultrafiltration apparatus was used in place of a dialysis tube. An ultrafiltration apparatus (PC Cassette System manufactured by Rhone Poulenc Co.) and a sulfonated polysulfone membrane (IRIS3026 manufactured by Rhone Poulenc Co.) were used as the diafiltration apparatus to purify the emulsion at a dilution rate of up to 5 times. The ultrafiltraion was conducted under the following conditions: total membrane area of 0.506 $m^2$ and average operation pressure of 0.5 to 3 $kgf/cm_2$. The same ultrafiltration apparatus and filtration membrane were also used in the following examples. The emulsion was diluted with distilled water to a nonvolatile component concentration of 5% by weight. A portion of the thus obtained sample was taken out, emulsion particles were filtrated with the ultrafiltration apparatus and the concentration of metal ions in the filtrate was measured using a desk-top plasma emission spectroscopic analyzer (SPS7700, manufactured by Seiko Denshi Kogyo Co.). The same measuring instrument was also used in the following examples. Most of the measured metal ions contained in the dispersing medium were sodium and potassium ions derived from the monomers and the polymerization initiator and other metal ions were rarely detected. Therefore, the quantity of only sodium and potassium ions was determined. The concentration of metal ions (Na+K) was found to be 230 ppm. The emulsion was transferred to a plastic container and kept in the dark at room temperature for about 3 months. As the result, no generation of mold was observed. The container used for observation was in advance cleaned with ethanol and dried to eliminate the effects of bacteria adhered in the container. The containers used in the following experiments were also cleaned before use.

The emulsion containing 5% by weight of a polymer prepared above and an aqueous solution of 3% by weight of oxalic acid (dihydrate) were kept in separate containers, and 0.05 g portions were taken out from these containers and mixed together just before use. The dental composition of the present invention thus prepared was used within 1 minute after the mixing to carry out evaluation on the effect of relieving hypersensitivity and durability. As the result, occlusion degrees of dentinal tubules after treatments (i) and (ii) were all 100% and that after 35 minutes of ultrasonic cleaning (treatment (iii)) in place of 5 minutes of ultrasonic cleaning of treatment (i) was about 40%.

The toothbrush abrasion resistance of a coating film formed on the surface of dentin and the occlusion of dentinal tubules can be checked by treatment (ii). However, since the diameter of the hair of a toothbrush is generally 100 to 400 μm, the occlusion durability of a coating film formed in a dentinal tubule cannot be evaluated. Although ultrasonic waves are not irradiated actually, 35 minutes of an ultrasonic exposure test (treatment (iii)) was made to evaluate the occlusion durability of the inside of a dentinal tubule.

Experiments on generation of mold and experiments on applicability of anitseptics Run No.1

An emulsion newly synthesized in the same manner as in Emulsion Synthesis Example and purified with a dialysis tube was diluted with distilled water to a nonvolatile component concentration of 5% by weight. A portion of the thus obtained sample was taken out, and emulsion particles were used for the measurement of the concentration of metal ions in the filtrate in the same manner as in Example 4. The concentration of metal ions (Na+K) was found to be 1,200 ppm. The emulsion was transferred to a plastic container with a lid and kept in the dark at room temperature for about 3 months. Black mold as large as 0.1 to 3 mm grew at many places in the emulsion.

Run No.2

The emulsion of Run No.1 containing 5% by weight of the polymer just after purification and an aqueous solution of 3% by weight of oxalic acid (dihydrate) were kept in separate containers and 0.05 g portions were taken out from these containers and mixed together just before use. The dental composition of the present invention thus prepared was used within 1 minute after the mixing to carry out evaluation on the effect of relieving hypersensitivity and durability. As the result, occlusion degrees of dentinal tubules after treatments (i) and (ii) were all 100% and that after treatment (iii) was 0%.

Run No.3

An emulsion newly synthesized in the same manner as in Emulsion Synthesis Example and purified with a dialysis tube was diluted with distilled water to a nonvolatile component concentration of 5% by weight. A portion of the thus obtained sample was taken out, and emulsion particles were used for the measurement of the concentration of metal ions in the filtrate in the same manner as in Example 4. The concentration of metal ions (Na+K) was found to be about 300 ppm. The emulsion was transferred to a plastic container with a lid and kept in the dark at room temperature for about 3 months. Black mold as large as 0.1 to 3 mm were grown at several places in the emulsion.

Run No.4

An emulsion was newly synthesized in the same manner as in Emulsion Synthesis Example and purified at a dilution rate of 0.3 time using a diafiltration apparatus. The emulsion was diluted with distilled water to a nonvolatile component concentration of 5% by weight. A portion of the thus obtained sample was taken out, and emulsion particles were used for the measurement of the concentration of metal ions in the filtrate in the same manner as in Example 4. The concentration of metal ions (Na+K) was found to be about 1,500 ppm. The emulsion was transferred to a plastic container with a lid and kept in the dark at room temperature for about 3 months. As the result, no growth of mold was observed. The results of evaluation on the effect of relieving hypersensitivity and evaluation on durability were all about 80% after treatments (i) and (ii) and 0% after treatment (iii). The effect of preventing the growth of mold obtained by using a diafiltration apparatus was confirmed by comparison between this run and Run No.3. However, the durability of the resulting coating film was insufficient.

Run No.5

An emulsion was newly synthesized in the same manner as in Emulsion Synthesis Example and purified at a dilution rate of 2 times using a diafiltration apparatus. The emulsion was diluted with distilled water to a nonvolatile component concentration of 5% by weight. A portion of the thus obtained sample was taken out, and the concentration of metal ions in the filtrate was measured in the same manner as in Example 4. The concentration of metal ions (Na+K) was found to be about 970 ppm. The emulsion was transferred to a plastic container with a lid and kept in the dark at room temperature for about 3 months. As the result, no growth of mold was observed. The results of evaluation on the effect of relieving hypersensitivity and evaluation on durability were all about 90% after treatments (i) and (ii) and about 20% after treatment (iii). Improvement in the durability of the resulting coating film by reducing the concentration of metal ions in the dispersing medium was confirmed by comparison between this run and Run No.4.

Run No.6

An emulsion was newly synthesized in the same manner as in Emulsion Synthesis Example and purified at a dilution rate of 5 times using a diafiltration apparatus. The emulsion was diluted with distilled water to a nonvolatile component concentration of 5% by weight. A portion of the thus obtained sample was taken out, and emulsion particles were used for the measurement of the concentration of metal ions in the filtrate in the same manner as in Example 4. The concentration of metal ions (Na+K) was found to be about 300 ppm. The emulsion was transferred to a plastic container and kept in the dark at room temperature for about 3 months. As the result, no growth of mold was observed. The results of evaluation on the effect of relieving hypersensitivity and evaluation on durability were all 100% after treatments (i) and (ii) and about 40% after treatment (iii).

Run No.7

A 10 g portion of the emulsion (metal ions: 970 ppm) of Run No.5 was put into a 20 cc brown glass bottle with a plastic screw lid as a sample, and 3 samples were prepared for the emulsion. Further, mold grown in the emulsion of Run No.1 was cut into 1 to 2 mm pieces and each piece was transplanted to each sample. After measuring the size of the mold with calipers, the mold was left to stand in the dark at room temperature for 2 months. As the result, the mold in one out of the three samples grew about 25% bigger, but the mold in the other two samples remained unchanged in size. This indicates that growth of bacteria such mold can be suppressed even when they have entered the emulsion after diafiltration.

Run No.8

A 10 g portion of the emulsion (metal ions: 300 ppm) of Run No.6 was put into a 20 cc brown glass bottle with a plastic screw lid as a sample, and 3 samples were prepared for the emulsion. Further, mold grown in the emulsion of Run No.1 was cut into 1 to 2 mm pieces and each piece was transplanted to each sample. After measuring the size of the mold with calipers, the mold was left to stand in the dark at room temperature for 1 to 2 months. As the result, the mold in all the three samples remained unchanged in size.

Run No.9

A 10 g portion of the emulsion (metal ions: 1,500 ppm) of Run No.4 was put into a 20 cc brown glass bottle with a plastic screw lid as a sample, and 3 samples were prepared for the emulsion. Further, mold grown in the emulsion of Run No.1 was cut into 1 to 2 mm pieces and each piece was transplanted to each sample. After measuring the size of the mold with calipers, the mold was left to stand in the dark at room temperature for 1 to 2 months. As the result, the mold in all the three samples grew bigger by 10 to 50%. This indicates that bacteria such as mold grow after they have entered the emulsion after diafiltration and impairs sanitation in the composition of the present invention. disadvantageously.

Run No.10

To the emulsion (metal ions: 1,500 ppm) of Run No.4 was added 3% by weight of 2-phenyl alcohol as an antiseptic, and mold was transplanted to the emulsion and left to stand in the dark at room temperature for 1 month as in Run No.7. No size expansion of the mold was observed in all the samples and the emulsion remained unchanged in state.

Run No.11

To the emulsion (metal ions: 1,500 ppm) of Run No.4 was added 0.3% by weight of benzoic acid as an antiseptic, and mold was transplanted to the emulsion and left to stand in the dark at room temperature for 1 month as in Run No.7. No size expansion of the mold was observed in all the samples and the emulsion remained unchanged in state.

Run No.12

To the emulsion (metal ions: 1,500 ppm) of Run No.4 was added 2% by weight of phenethyl alcohol as an antiseptic, and mold was transplanted to the emulsion and left to stand in the dark at room temperature for 1 month as in Run No.7. No size expansion of the mold was observed in all the samples and the emulsion remained unchanged in state.

Run No.13

To the emulsion (metal ions: 1,500 ppm) of Run No.4 was added 0.5% by weight of salicylic acid as an antiseptic, but the salicylic acid did not dissolve in the emulsion.

Run No.14

To the emulsion (metal ions: 1,500 ppm) of Run No.4 was added 0.5% by weight of formaldehyde as an antiseptic, but the emulsion agglomerated within 1 week.

Run No.15

To the emulsion (metal ions: 1,500 ppm) of Run No.4 was added 0.5% by weight of glutaraldehyde as an antiseptic, but the emulsion agglomerated within 1 week.

Run No.16

To the emulsion (metal ions: 1,500 ppm) of Run No.4was added 0.5% by weight of zinc-bis-(2-pyridinethiol-1-oxide) bis-(2-pyridylthio)zinc-1,1'-dioxide(Zinc Pyrithione) as an antiseptic, but the emulsion agglomerated immediately.

What is claimed is:

1. A dental composition for relieving dentin hypersensitivity comprising (A) an aqueous emulsion component (1) which contains, as emulsion particles, polymer particles having a diameter smaller than that of a dentinal tubule and forming an agglomerate larger than the diameter of a dentinal tubule when they react with a calcium compound and (2) which has a metal ion concentration in a dispersing medium of 1,000 ppm or less purified by a diafiltration method using an ultrafiltration apparatus, and (B) a water-soluble organic acid component or a water-soluble salt component thereof, wherein the reaction product of the organic acid component or the water-soluble salt component with calcium produces a calcium salt which is water insoluble or hardly soluble in water.

2. The dental composition of claim 1, wherein the proportion of the component (A) is 50 to 99.5 parts by weight based on 100 parts by weight of the total of the components (A) and (B).

3. The dental composition of claim 1, wherein the proportion of a polymer contained in the component (A) is 0.1 to 60 parts by weight, in terms of a solid content, based on 100 parts by weight of the dental composition.

4. The dental composition of claim 1, wherein the emulsion particles of the polymer contained in the component (A) include particles having a particle diameter of less than 3 μm.

5. The dental composition of claim 1, wherein the component (A) is an emulsion of a polymer having at least one functional group which is capable of reacting with a calcium compound and selected from the group consisting of a carboxyl group, a group having at least one hydroxyl group bonded to a phosphorus atom and a sulfonic acid group.

6. The dental composition of claim 1, wherein the component (A) is an emulsion of a copolymer consisting of an alkyl (meth)acrylate component and a styrene sulfonic acid component.

7. The dental composition of claim 1, wherein the component (B) is at least one water-soluble oxalic acid compound selected from the group consisting of oxalic acid, and metal salts, ammonium salts and amine salts of oxalic acid.

8. The dental composition of claim 1, which further contains (C) at least one antiseptic component selected from inorganic and organic antiseptics.

* * * * *